United States Patent [19]
Rogers

[11] Patent Number: 4,750,931
[45] Date of Patent: Jun. 14, 1988

[54] CERTAIN 3,5-DISUBSTITUTED-2-PYRIDYLOXY-FLUOROPHENOXY-ALKANOIC ACIDS, DERIVATIVES THEREOF AND HERBICIDAL PROPERTIES

[75] Inventor: Richard B. Rogers, Midland, Mich.

[73] Assignee: The Dow Chemical Company, Midland, Mich.

[21] Appl. No.: 787,824

[22] Filed: Oct. 15, 1985

Related U.S. Application Data

[63] Continuation-in-part of Ser. No. 550,328, Nov. 10, 1983, abandoned.

[51] Int. Cl.$^4$ .................... C07D 213/64; A01N 43/40
[52] U.S. Cl. ........................................ 71/94; 546/153; 546/271; 546/291; 546/301; 546/302; 548/169; 544/354; 544/356; 560/61; 560/62

[58] Field of Search .................... 546/301, 302; 71/94

[56] References Cited

U.S. PATENT DOCUMENTS 4,267,336  5/1981  Nishiyama et al. .................. 546/302
4,401,459  8/1983  Satomi et al. ............................ 71/94

*Primary Examiner*—Alan L. Rotman
*Attorney, Agent, or Firm*—Merlin B. Davey

[57] ABSTRACT

Certain novel fluorophenoxy compounds, principally aryloxyfluorophenoxyalkanoic acids and derivatives thereof, are described. More specifically, these novel compounds bear 1 to 4 fluorine substituents on the phenyl ring. These novel compounds exhibit surprising preemergent and postemergent activity when used according to the method of the invention in the control of grassy weeds.

15 Claims, No Drawings

CERTAIN 3,5-DISUBSTITUTED-2-PYRIDYLOXY-FLUORO-PHENOXY-ALKANOIC ACIDS, DERIVATIVES THEREOF AND HERBICIDAL PROPERTIES

CROSS-REFERENCE TO RELATED APPLICATION

This application is a continuation-in-part of Application Ser. No. 550,328 field Nov. 10, 1983, now abandoned.

BACKGROUND OF THE INVENTION

1. Field of the Invention

This invention relates (a) to novel fluorophenoxy compounds, (b) to herbicidal compositions of such novel compounds and (c) to methods of using such compounds for the preemergent and postemergent control of grassy weeds in non-crop areas as well as in the presence of certain valuable crops such as soybeans, cotton and wheat.

2. Description of the Prior Art

Belgian Pat. No. 834,495, issued Feb. 2, 1976, as well as the published German patent application equivalent thereto, viz., No. 2,546,251, published Apr. 29, 1976, describe 2-((4-pyridinyl-2-oxy)phenoxy)alkanoic acids, salts and esters having halo substitution in the 3- and/or 5-ring positions in the pyridine ring.

Later references, e.g. published British Patent application 2,026,865 disclose such compounds having trifluoromethyl substitution on the pyridine ring and European Patent 0002800 describes the enhanced effect of the D-stereoisomers of such compounds.

SUMMARY OF THE INVENTION

The present invention is directed to novel fluorophenoxy compounds having herbicidal activity and which correspond to the formula

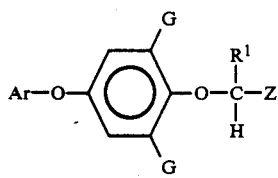

wherein Ar is a substituted or unsubstituted aromatic or heteroaromatic ring system, preferably containing from 6 to 10 atoms, G is H or F with the proviso that at least one G is F, $R^1$ is a $C_1$–$C_3$ alkyl group and Z is an organic moiety containing N, O or S atoms or a metallic, ammonium or organic amine cation and is or can be hydrolyzed and/or oxidized in plants or soil to a carboxyl moiety that is in undissociated and/or dissociated form. The invention is also directed to the novel stereoisomers of such compounds, the R-isomers having exceptional activity.

A variety of herbicidal compounds containing substituted pyridyl and phenoxy moieties joined via a bivalent —O— or —S— are described in the art. For example, U.S. Pat. Nos. 4,046,553; 4,317,913; 4,267,336; 4,213,774; 4,324,627 and 4,309,547; U.S. patent application Ser. Nos. 262,063 and 261,109, both filed July 30, 1980; U.S. patent application Ser. No. 765,401, filed Aug. 12, 1985; European Patent 483 and European Patent Applications 1473; 4433; 75,840 and 83,556 all describe such compounds, methods of making them, compositions containing them and methods of utilizing said compositions. These teachings are incorporated herein by reference. In general, the moieties bonded to the pendant —O— groups of the phenoxy in the herbicidal compounds described in these references will also be suitable as the monovalent organic radicals represented by Ar and Z in the formula for the aforementioned novel compounds and, given the appropriate starting materials, the compounds of this invention can be prepared by methods described in the above-mentioned prior art, and can be utilized in compositions as described in said prior art.

In the following, the term halogen is understood to include fluorine (F), chlorine (Cl), bromine (Br) and iodine (I).

Ar moieties include, but are not limited to,

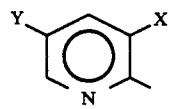

wherein X is hydrogen or halogen and Y is halogen, $CF_3$, $CHF_2$ or $CClF_2$;

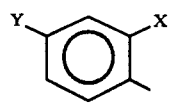

wherein X and Y are as above defined;

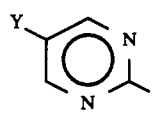

wherein Y is halogen or $CF_3$;

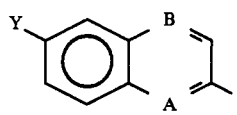

wherein Y is halogen or $CF_3$, and A and B are N or CH;

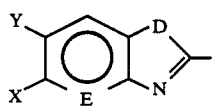

where X and Y are independently hydrogen, halogen, and $CF_3$;
D is S or O and
E is N or CH, and

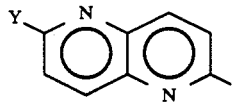

wherein Y is halogen or $CF_3$.

Z moieties include, but are not limited to $-(J)_nR^2$ wherein J is a substituted or unsubstituted saturated or unsaturated alkyl group containing an even number of carbon atoms, preferably from 2 to 18 carbon atoms, or a structure such as $$-\overset{O}{\underset{\|}{C}}-CH_2-, \quad -\overset{OR^3}{\underset{|}{CH}}-CH_2- \quad or \quad -\overset{OR^3}{\underset{|}{C}}=CH-,$$

n is 0 or 1, and $R^2$ is selected from moieties corresponding to one of the following formulae:

$-CN,$ (1)

$-C\begin{smallmatrix}N-NH\\ \|\quad\|\\N\diagdown N\end{smallmatrix}$ (2)

$-C\begin{smallmatrix}NH-N\\ \|\quad\|\\N\diagup N\end{smallmatrix}$ (3)

$-\overset{O}{\underset{\|}{C}}-X,$ (4)

wherein X is halogen, or CN, $-\overset{O}{\underset{\|}{C}}-O^-M^+,$ (5)

wherein M is a metallic cation, ammonium or an organic amine cation typically, but not exclusively, containing alkyl (saturated or unsaturated), alicyclic, heterocyclic or aromatic groups, all unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl, $-CH_2OR^3,$ (6)

$-\overset{O}{\underset{\|}{C}}-R^3,$ (7)

$-CH_2O-\overset{O}{\underset{\|}{C}}-R^6,$ (8)

$-\overset{O}{\underset{\|}{C}}-OR^3,$ (9)

$-\overset{O}{\underset{\|}{C}}-SR^3,$ (10)

$-\overset{O/S}{\underset{\|}{C}}-N\overset{R^4}{\underset{R^3}{\diagdown}},$ (11)

$-CH_2O-\overset{O/S}{\underset{\|}{C}}-N\overset{R^4}{\underset{R^3}{\diagdown}},$ (12)

$-\overset{O/S}{\underset{\|}{C}}-N\overset{R^5}{\underset{SO_2R^6}{\diagdown}},$ (13)

$-\overset{O/S}{\underset{\|}{C}}-N\overset{R^3}{\underset{CN}{\diagdown}},$ (14)

$-CH_2O-\overset{O/S}{\underset{\|}{C}}-N\overset{R^3}{\underset{CN}{\diagdown}},$ (15)

$-\overset{W}{\underset{|}{C}}=N-R^3,$ (16)

$-\overset{R^4\diagdown\;\;\diagup R^3}{\underset{|}{N}}\atop{-C=N-R^3},$ (17)

$-\overset{O}{\underset{\|}{C}}-\overset{H/alkyl}{\underset{|}{N}}OR^3,$ (18)

$-\overset{O/S}{\underset{\|}{C}}-\overset{R^4}{\underset{|}{N}}-N\overset{R^4}{\underset{R^3}{\diagdown}},$ (19)

$-\overset{O/S}{\underset{\|}{C}}-\overset{R^4}{\underset{|}{N}}-N\overset{R^3}{\underset{CN}{\diagdown}},$ (20)

$-\overset{O/S}{\underset{\|}{C}}-\overset{R^4}{\underset{|}{N}}-N\overset{R^5}{\underset{SO_2R^6}{\diagdown}},$ (21)

$-\overset{O/S}{\underset{\|}{C}}-\overset{R^3}{\underset{|}{N}}-\overset{O}{\underset{\|}{C}}-R^3,$ (22)

$-C\overset{OR^6}{\underset{OR^6}{\diagdown}}OR^6,$ (23)

$-C(SR^6)_3,$ (24)

$-\overset{H}{\underset{|}{C}}(OR^6)_2,$ (25)

$-\overset{H}{\underset{|}{C}}(SR^6)_2,$ (26)

(27)
[cyclic acetal with $R^7$, O, O, C—H]

-continued

(28) 

(29) 

(30) 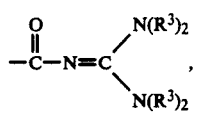

(31) 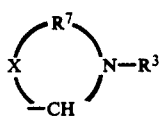

where X is S or O,
where W is halogen, alkoxy or alkylthio; $R^3$ is H or $R^6$; $R^4$ is H, alkoxy or $R^6$; $R^5$ is H, a metallic cation or $R^6$; and $R^6$ is an alkyl (saturated or unsaturated), alicyclic, heterocyclic or aromatic group, unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl,

(32) 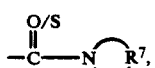

(33) 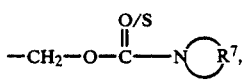

(34) 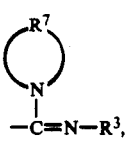

(35) 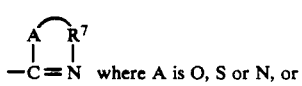

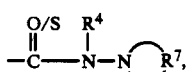 where A is O, S or N, or

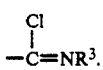

wherein $R^7$ completes an unsubstituted or substituted saturated heterocyclic ring system.

The above derivatives can be made by processes generally known to those skilled in the art and as described in the above-mentioned patents. For example, the corresponding acid chlorides can be reacted with a Grignard reagent to make the desired ketone derivative. Similarly, reaction of an acid chloride with KSH will provide the desired thiol acid. Thioamides may be prepared from the corresponding amide by reaction with $P_2S_5$ or, if hydrogen is present on the nitrogen atom, the carbonyl may be converted to, e.g., chloride, with removal of HCl, followed by reaction with hydrogen sulfide. Carbamoyl chlorides are available in the art or they may be prepared from the desired amine and phosgene or thiophosgene for use in making compounds containing the

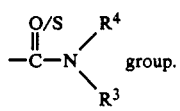 group.

The reaction of an amine with a sulfonyl chloride, e.g., $R^5NH_2 + R^6SO_2Cl$ provides the group

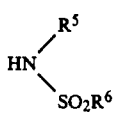

for use in reacting with an appropriate acid chloride.
The reaction of an amine with BrCN provides, e.g.,

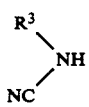

which reacts with the appropriate acid chloride to provide compounds containing the

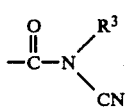

moiety. $P_2S_5$ is employed to make the corresponding S-containing compound.

Reaction of the above cyanoamine with phosgene or thiophosgene provides

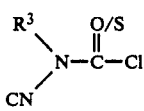

for use in making the corresponding derivatives.
The reaction of the compounds having the moiety

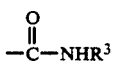

with $PCl_5$ will provide compounds having the moiety $$\overset{Cl}{\underset{|}{-C}}=NR^3.$$

The reaction of the corresponding acid chloride with $RONH_2$ will provide compounds having the group

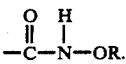

Various hydrazine derivatives can be made, e.g., from trimethyl hydrazine by reaction with the acid chlorides. The reaction of the amides, e.g.,

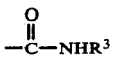

with dicarboxylic anhydrides will provide compounds having the group

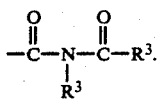

$R^2$ is preferably a carboxylic acid group, an alkali or alkaline earth metal salt thereof, an ammonium or organic amine salt thereof, a lower alkyl ester thereof, wherein "lower alkyl" includes straight, branched or cyclic saturated or unsaturated alkyl groups containing no more than 8 carbon atoms, or an agriculturally acceptable amide such as a lower monoalkyl or substituted aromatic amide. Preferably, n is 0.

In the above formulae the aliphatic groups preferably contain 1 to 8 carbon atoms, the alkenyl and alkynyl groups preferably contain 2 to 8 carbon atoms, the alicyclic groups preferably contain 3 to 8 carbon atoms and the aromatic moiety is preferably phenyl, although other ring systems, including heterocyclic ring systems, may be employed if desired.

In the formula for the aforementioned novel compounds, X is advantageously Cl, Br, or F, Y is advantageously $CF_3$, except in the case of pyrimidine where Y is advantageously I, $R^1$ is advantageously $CH_3$ and Z is advantageously

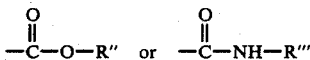

wherein R'' is methyl, ethyl, propyl, isopropyl, isobutyl or n-butyl, and R''' is R'' or

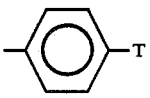

such that T is halogen, $-CF_3$, $-OCF_3$, $-OCF_2CF_2H$, $-OCH_2CF_3$, or $-OCF_2CCl_2H$.

The compounds of the above formula, hereinafter referred to for convenience as "active ingredients", have been found to be especially active as herbicides for the control of undesired vegetation, for example, grassy or graminaceous weeds and are unexpectedly more effective than the compounds of the known art. With the compounds of this invention, it is possible to employ lower dosage rates and still obtain effective control, thus reducing plant residues and any potential environmental contamination and/or toxicological effect on fish and warm blooded animals. Accordingly, the present invention also encompasses herbicidal compositions containing one or more of these active ingredients as well as preemergent and postemergent methods of controlling undesired plant growth, especially in the presence of valuable crops. Such methods comprise applying a herbicidally-effective amount of one or more of said active ingredients to the locus of the undesired plants, that is, the seeds, foliage, rhizomes, stems and roots or other parts of the growing plants or soil in which the plants are growing or may be found.

The compounds of this invention are normally applied in the form of an agricultrually acceptable salt, ester or amide wherein the terms "salt, ester or amide" are meant to include any salt, ester or amide or derivative of the acid which is or can be hydrolyzed and/or oxidized in plants or soil to a carboxyl moiety (acid) that is in undissociated or dissociated form, the acid being the active herbicidal agent in the plants.

The method of this invention comprises providing in undesirable grassy plants a herbicidally effective amount of a compound having the formula

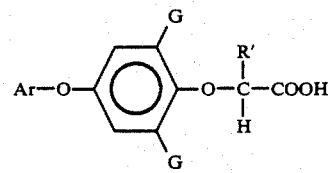

wherein Ar, G, and R' are as above defined.

DETAILED DESCRIPTION OF THE INVENTION

The term "herbicide" is used herein to mean an active ingredient which controls or adversely modifies the growth of plants because of phytotoxic or other effects substantial enough to seriously retard the growth of the plant or further to damage the plant sufficiently to kill the plant.

By "growth controlling" or "herbicidally-effective" amount is meant an amount of active ingredient which causes a modifying effect and includes deviations from natural development, killing, regulation, desiccation, retardation, and the like.

The term "plants" is meant to include germinant seeds, emerging seedlings, rhizomes, stolons and other underground propagules, and established vegetation.

The active ingredients, i.e., new compounds, of the present invention are readily prepared by processes described in the above cited prior art and as illustrated in the following examples by choosing the appropriate starting materials. The stereoisomers are readily separated as described in European Patent 2800 referred to above.

Certain of the reactants employed to make the novel compounds of this invention are themselves novel compounds and such reactants may be made as generally described hereafter and as specifically set forth in the following examples or by methods analagous thereto, starting with known compounds.

EXAMPLE 1

Preparation of 2-(4-((3-chloro-5-trifluoromethyl-2-pyridinyl)-oxy)-2-fluorophenoxy)propanoic acid A. 2-Fluoro-4-nitrophenol To a stirred solution of 2-fluorophenol (32.3 g, 0.288 mole) in methylene chloride which was cooled to $-10°$ C. (ice-salt bath), was slowly added 90 percent nitric acid (22 g, 0.31 mole $HNO_3$) over a one-hour period. During the addition, the temperature was maintained at about −5° C. After the addition was complete, stirring was continued at 0° C. for an additional hour. At the end of this period, the precipitate which had formed was filtered and washed with several portions of cold methylene chloride. G.C. and thin-layer chromatography (silica gel, 7:3 hexane-acetone) showed that this material was essentially a single compound and was the more polar and less volatile of the two products which formed in the reaction. This solid was taken up in ether, washed with water, dried ($MgSO_4$) and the solvent evaporated. The resulting solid was recrystallized from methylcyclohexane to give 13 g of a light yellow solid: m.p.=119°-121° C. NMR ($CDCl_3$) showed this to be the desired 2-fluoro-4-nitrophenol. The methylene chloride mother liquor was washed with water, dried ($MgSO_4$) and the solvent evaporated. The solid which resulted was triturated with boiling hexane (3×150 ml). This effectively removed all of the least polar-more volatile reaction product. This hexane solution was treated with charcoal, filtered, concentrated to about 300 ml and cooled to give 13.5 g (30 percent) of by-product 2-fluoro-6-nitrophenol as a yellow solid: m.p.=70°-86° C.

B. Methyl 2-(2-fluoro-4-nitrophenoxy)propanoic acid

A stirred mixture of 2-fluoro-4-nitrophenol (15.7 g, 0.1 mole), methyl 2-bromopropionate (16.7 g, 0.1 mole), and potassium carbonate (18.1 g, 0.13 mole) in DMSO (150 ml) was heated at 100° C. (bath temperature) for 45 minutes. After cooling, the mixture was poured into ice-water (1000 ml) and the resulting mixture extracted with ether (3×200 ml). The ether fractions were combined, pentane (150 ml) added, and the resulting solution washed with water. The organic phase was dried ($MgSO_4$) and the solvent evaporated to give 22.5 g (92.6 percent) of the desired phenoxypropionate as a yellow liquid. This material solidified upon standing. Recrystallization from ether-hexane gave an off-white cyrstalline solid: m.p. 53°-55° C.; NMR ($CDCl_3$) was consistent with the assigned structure.

| Analysis: | C | H | N |
|---|---|---|---|
| Calculated: | 49.39 | 4.14 | 5.76 |
| Found: | 49.40 | 4.08 | 5.81 |

C. Methyl 2-(4-amino-2-fluorophenoxy)propanoate

To a solution of the nitrophenoxypropionate prepared in B (16.6 g, 0.068 mole) in ethanol (200 ml) was added 5 percent Pd/C (1.5 g). This solution was hydrogenated on a Paar shaker (initial $H_2$ pressure=50 psi). Hydrogen was taken up very rapidly in an exothermic reaction—the theoretical amount being consumed in less than 5 minutes. The mixture was degassed with $N_2$, filtered through celite, and the solvent evaporated to give a quantitative yield of the desired aniline as a nearly colorless oil which darkened upon standing. R.I.=1.5189 at 25° C.; NMR ($CDCl_3$); $^1H$ and $^{19}F$ were consistent with the assigned structure. This material was used directly in the next reaction.

D. The above prepared aniline (14 g, 0.066 mole) was added to a solution of concentrated HCl (25 ml) in water (75 ml) and the resulting solution cooled to about 5° C. in an ice bath. To this mechanically stirred slurry was slowly dropped a solution of sodium nitrite (4.83 g, 0.07 mole) in water (10 ml). The temperature was maintained at about 7° C. during the addition. By the time the addition was complete, the reaction mixture was homogeneous. After 15 minutes of additional stirring, charcoal was added and the cold mixture filtered through celite. The filtrate was added to a 1000 ml erlenmeyer flask equipped with a mechanical stirrer and cooled in an ice bath. To this vigorously stirred solution, a solution of sodium fluoroborate (14.27 g, 0.13 mole) in water (20 ml) was added all at once. The mixture was stirred for 30 minutes, during which time a solid slowly separated. This solid was filtered, washed with several portions of ice water then dried in a vacuum oven over $P_2O_5$ for several hours at 50° C. to give 15.75 g (76.5 percent) of the diazonium tetrafluoroborate: m.p.=122°-124° C.; NMR ($CF_3CO_2H$) was consistent with the assigned structure.

E. Methyl 2-(2-fluoro-4-hydroxyphenoxy)propanoate

To stirred trifluoroacetic acid (150 ml) was carefully added potassium carbonate (18.08 g, 0.13 mole). After $CO_2$ evolution ceased, the above tetrafluoroborate diazonium salt (15.75 g, 0.05 mole) was added and the resulting mixture stirred and heated at reflux for 72 hours. The reaction was followed by NMR. After cooling, excess trifluoroacetic acid was evaporated and water (350 ml) added to the residue. The resulting dark mixture was stirred at room temperature for 3 hours, then extracted with ether (3×200 ml). The ether phases were combined, dried ($MgSO_4$) and the solvent evaporated to give a dark viscous oil (∼10 g). NMR of this material showed that the methyl ester of the propionate had been hydrolyzed. The oil was taken up in methanol (400 ml), sulfuric acid (1 g) added and the solution heated at reflux for 3 hours. Most of the methanol was evaporated and water added to the residue. This mixture was extracted with ether (3×150 ml), the ether extracts were combined, dried ($MgSO_4$) and the solvent evaporated. G.C. showed that 3 volatile materials were present in the ratio (peak areas) of 15:4:81 with the second peak being a shoulder off the first peak. The mixture was subjected to Kugelrohr distillation. Two fractions were collected: (1) everything up to ∼110° C. (oven temperature). This consisted of essentially the first two G.C. peaks but contained a trace of peak 3. (2) Everything distilling between 110°-140° C. This consisted exclusively of peak 3 and was shown to be the desired methyl 2-(2-fluoro-4-hydroxyphenoxy)propanoate: 5.5 g (51 percent); NMR ($CDCl_3$) was consistent with the assigned structure; R.I.=1.5044 at 25° C.—yellow oil.

| Analysis: | C | H |
|---|---|---|
| Calculated: | 56.07 | 5.18 |
| Found: | 54.94 | 5.16 |

F. A stirred solution of 2-fluoro-3-chloro-5-trifluoromethylpyridine (2.33 g, 0.0117 mole), the above prepared phenol (2.5 g, 0.0117 mole), and potassium carbonate (2.1 g, 0.015 mole) in DMSO (25 ml) was heated at 125°-140° C. (pot temperature) for 30 minutes, cooled, and poured into water (250 ml). The resulting solution was extracted with ether (3×100 ml). The ether phases were combined, treated with charcoal, then $MgSO_4$, filtered and the solvent evaporated to give the desired pyridyloxyphenoxypropanoate as a light yellow oil (4.0 g, 87 percent): NMR (CDCl₃) was consistent with the assigned structure; R.I.=1.5120 at 25° C.

| Analysis: | C | H | N |
|---|---|---|---|
| Calculated: | 48.81 | 3.07 | 3.56 |
| Found: | 48.58 | 3.02 | 3.54 |

EXAMPLE 2

Preparation of 2-(4-((3-Fluoro-5-chloro-2-pyridinyl)-oxy)-2-fluorophenoxy)propanoate A stirred mixture of 2,3-difluoro-5-chloropyridine (1.40 g, 0.0093 mole), the above phenol (1E) (2.0 g, 0.0093 mole) and potassium carbonate (1.39 g, 0.01 mole) in DMSO (20 ml) was heated at 140°-150° C. (oil bath temperature) for 30 minutes, then cooled and poured into water (200 ml). The resulting mixture was extracted with ether (3×100 ml). The ether extracts were combined, and pentane (50 ml) added. This solution was washed with water (200 ml), treated with charcoal, then with MgSO₄, filtered and the solvent evaporated to give the desired pyridyloxyphenoxypropionate as a light yellow oil (2.6 g, 83 percent): NMR (CDCl₃) was consistent with the assigned structure; R.I.=1.5349 at 25° C.

| Analysis: | C | H | N |
|---|---|---|---|
| Calculated: | 52.41 | 3.52 | 4.08 |
| Found: | 52.26 | 3.47 | 3.93 |

EXAMPLE 3

Preparation of Methyl 2-(2-fluoro-4-((3-fluoro-5-trifluoromethylpyridinyl)-2-oxy)phenoxy)propanoate A stirred solution of methyl 2-(2-fluoro-4-hydroxyphenoxy)propanoate (2.0 g, 9.34 mole), 2,3-difluoro-5-trifluoromethylpyridine (1.71 g, 9.34 mole), and potassium carbonate (2.13 g, 15.3 mole) in dimethyl sulfoxide (40 ml) was heated at 70° C. for 20 hours. After cooling, diethyl ether (100 ml) was added and the resultant mixture was stirred for five minutes. It then was filtered. The filtrate was washed sequentially with 2N HCl (2×100 ml) then water (3×100 ml). The separated ether phase was then dried (MgSO₄), filtered and the ether removed by distillation. A yellow oil weighing 2.8 grams (79 percent) resulted. R.I.=1.4932 @ 25° C. NMR spectroscopy (¹H, ¹⁹F) confirmed the structure as the consistent with the assigned structure for the title product. The carbon, hydrogen and nitrogen content was as follows:

| Analysis: | % C | % H | % N |
|---|---|---|---|
| Calculated: | 50.93 | 3.21 | 3.71 |
| Found: | 50.78 | 3.26 | 3.89 |

In a similar manner, the following derivatives were prepared:

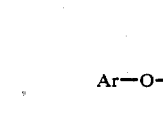

| Ar | RI or MP | Calc'd | Found |
|---|---|---|---|
| 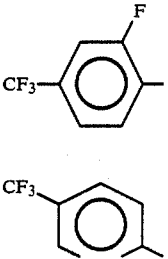 | 1.4923 | C 54.26<br>H 3.49 | C 54.46<br>H 3.47 |
| 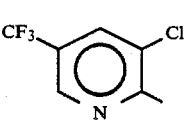 | 1.4994 | C 53.48<br>H 3.65<br>N 3.90 | C 54.02<br>H 3.67<br>N 3.89 |
| 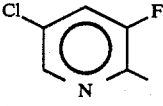 | 1.5120 | C 48.80<br>H 3.08<br>N 3.56 | C 48.58<br>H 3.02<br>N 3.54 |
| 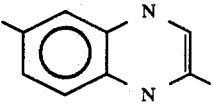 | 1.5349 | C 52.41<br>H 3.52<br>N 4.06 | C 52.26<br>H 3.47<br>N 3.93 |
| 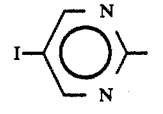 | 143-144° C. | C 57.37<br>H 3.75<br>N 7.44 | C 57.08<br>H 3.87<br>N 7.71 |
| 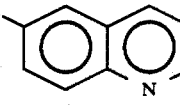 | 71-73° C. | C 39.98<br>H 2.87<br>N 6.61 | C 40.21<br>H 2.90<br>N 6.70 |
| 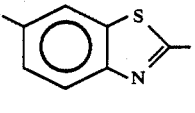 | 109-110° C. | C 61.42<br>H 4.24<br>N 3.66 | C 60.72<br>H 4.03<br>N 3.73 |
| 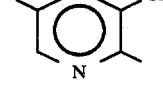 | 114-115° C. | C 52.98<br>H 3.34<br>N 3.69 | C 53.47<br>H 3.43<br>N 3.69 |
| 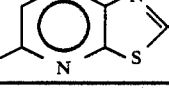 | 1.5587 | C 50.00<br>H 3.36<br>N 3.89 | C 40.76<br>H 3.17<br>N 3.85 |
|  | 103.5-104° C. | C 50.20<br>H 3.16<br>N 7.32 | C 49.78<br>H 3.04<br>N 7.48 |

EXAMPLE 4

Preparation of Methyl 2-(2-fluoro-4-(4-bromo-2-fluorophenoxy)phenoxy)-propanoate

A. Methyl 2-(2-fluoro-4-(2-fluoro-4-nitrophenoxy)phenoxy)-propanoate

To a stirred mixture of methyl 2-(2-fluoro-4-hydroxyphenoxy propanoate (4.0 g, 0.019 mole), potassium carbonate (2.9 g, 0.021 mole) and dimethyl sulfoxide (25 ml), was added 3,4-difluoronitrobenzene (3.0 g, 0.019 mole), all at once. The temperature was raised to 50° C., and held there for 19 hours. After this time, the resultant mixture was cooled to room temperature, then diethyl ether (50 ml) was added. This was filtered, and the filtrate was diluted with additional diethyl ether (150 ml). The latter solution was washed with 2N HCL (2×100 ml), then water (3×100 ml). After drying (MgSO4) and filtering, the diethyl ether was rmoved by distillation. A brown viscous oil resulted (6.2 grams, 92 percent). NMR spectroscopy ($^1$H, $^{19}$F) confirmed the structure as consistent with the structure for the desired product. It was used directly in the next step without further purification.

B. Methyl 2-(4-(4-amino-2-fluorophenoxy)-2-fluorophenoxy)-propanoate

A mixture of methyl 2-(2-fluoro-4-(2-fluoro-4-nitrophenoxy)phenoxy)propanoate (6.5 g, 0.018 mole) in ethanol (150 ml) containing 5 percent palladium on charcoal (0.5 g) as catalyst was subjected to hydrogenation (initial pressure equals 50 psi) on a Parr apparatus. After 19 hours, the excess hydrogen was removed and nitrogen was bubbled through the liquid mixture. This mixture was filtered through celite and the ethanol removed by distillation. A slightly yellow oil weighting 5.8 grams (98 percent) resulted.

NMR spectroscopy ($^1$H, $^{19}$F) and infrared (I.R.) spectroscopy confirmed the structure as one being consistent with the desired product. It was used directly in the next step without further purification.

C. Methyl 2-(2-fluoro-4-(4-bromo-2-fluorophenoxy)phenoxy)-propanoate

To a stirred mixture of methyl 2-(4-(4-amino-2-fluorophenoxy)-2-fluorophenoxy)propanoate (5.7 g, 0.018 mole), cuprous bromide (2.9 g, 0.01 mole), and hydrobromic acid (48 percent, 30 ml) cooled to less than 10° C. was added a solution of sodium nitrite (1.5 g, 0.022 mole) in 10 ml of water. Stirring was continued for 15 minutes at 8°-10° C. The temperature was raised after the lattter time to 60° C., and held there for one half hour. The resultant mixture was cooled to room temperature, then extracted with ether (3×50 ml). This ether extract was washed with water (3×50 ml), dried (MgSO4), filtered, and the ether removed by distillation. The resultant brown oil was diluted with methanol (50 ml), to which sulfuric acid (0.2 gram) was added. This solution was heated at reflux for one and one half hours. The methanol was evaporated and the resultant red-brown oil was dissolved in ether (50 ml). This was washed with water (3×50 ml), treated with charcoal, then filtered through a short pad of silica gel. Evaporation of the ether gave 1.8 g (26 percent) of a viscous amber oil: Refractive index=1.5472 @ 25° C. NMR spectroscopy ($^1$H, $^{19}$F) confirmed that the structure was consistent with the desired product. The carbon and hydrogen content was as follows:

|  | % C | % H |
| --- | --- | --- |
| Calculated | 49.63 | 3.43 |
| Found: | 50.19 | 3.36 |

EXAMPLE 5

Preparation of Methyl 2-(2,6-difluoro-4-((3-fluoro-5-trifluoromethyl-pyridinyl)-2-oxy)phenoxy)propanoate

A. 4-Bromo-2,6-difluorophenol

A stirred mixture of 2,6-difluorophenol (20.0 g, 0.154 mole), bromine (25.57 g, 0.16 mole) and powdered iron (1 g) in methylene chloride (250 ml) was heated at reflux overnight. The cooled reaction mixture was poured into ice-water (300 ml) containing sodium bisulfite (5 g) and the organic phase separated. The aqueous phase was washed with additional methylene chloride. The organic phase was combined, dried (MgSO4) and the solvent evaporated to give a light yellow oil which solidified upon standing. NMR (CDCL3) of this material was consistent with the assigned structure. No additional analysis or purification was attempted. This material was used directly in the next step.

B. 4-Benzyloxy-3,5-difluorobromobenzene

A stirred mixture of 4-bromo-2,6-difluorophenol (36 g, 0.172 mole), benzylchloride (21.77 g, 0.172 mole), and potassium carbonate (25 g, 0.18 mole) in demethylformamide (300 ml) was heated at 80°-90° for four hours. After cooling, the solvent was evaporated and ether added to the residue. The insoluble inorganic salts were removed by filtration, and solvent evaporated from the filtrate. The oily residue was subjected to bulb-to-bulb vacuum distillation on Kugelrohr apparatus to give the desired product as a nearly colorless oil (41 g, 80 percent): R.I.=1.5602 @ 25° C.; NMR (CDCl3) was consistent with the assigned structure.

| Analysis: | C | H |
| --- | --- | --- |
| Calculated | 52.20 | 3.03 |
| Found | 51.74 | 2.99 |

C. 4-Benzyloxy 3,5-difluorophenol

A stirred solution of 4-benzyloxy-3,5-difluoro-bromobenzene (9.87 g, 0.033 mole) in ether (100 ml) under an atmosphere of argon was cooled to less than 31 70° C. in a dry ice-acetone bath. To this solution was slowly added a solution of butyllithium in hexane (1.5M, 22 ml, 0.033 moles). Stirring was continued for 30 minutes after the addition was complete. In a separate apparatus, a stirred solution of trimethylborate (3.1 g, 0.033 mole) in ether (50 ml) under an atmosphere of argon was cooled to less than −70° C. The freshly prepared benzyloxyphenyllithium formed in the first reaction solution was slowly transferred to the trimethylborate/ether solution by way of a double-tipped stainless steel needle. The addition was at such a rate that the reaction temperature was maintained at less than −66° C. After the addition was complete, the temperature was allowed to rise to room temperature. At this point, 10 percent hydrochloric acid (25 ml) was carefully added. After stirring an additional 15 minutes, the aqueous phase was separated and discarded. The organic phase was treated with 10 percent hydrogen peroxide (20 ml) and the resulting mixture stirred and heated at reflux for 24 hours. After cooling, the aqueous phase was separated and discarded. The organic layer was washed with 10 percent ferrous ammonium sulfate (25 ml), then with water (50 ml). After drying (MgSO$_4$), the ether was evaporated to yield a brown oil (7.1 g, 91 percent) which solidified upon standing. G.C. showed that this material was approximately 92 percent pure. The proton and fluorine NMR spectra were consistent with the desired structure. Recrystallization of this material from hexane/ether gave a partially purified sample: m.p.=42°-44° C. It was used without additional purification.

D.
2-(4-Benzyloxy-3,5-difluorophenoxy)-3-fluoro-5-trifluoromethylpyridine A stirred mixture of the benzyloxyphenol (3.0 g, 0.0127 mole), 2,3-difluoro-5-trifluoromethylpyridine (0.013 mole) and potassium carbonate (1.81 g, 0.013 mole) in DMF (25 ml) was heated at 90°-100° for two hours. After cooling, the solvent was evaporated. Ether (100 ml) was added to the residue and the inorganic salts removed by filtration. The ether phase was treated with charcoal, then filtered through a short pad of silica gel. Evaporation of the ether gave a nearly colorless oil which solidified to a white solid upon standing. An analytical sample prepared by recrystallization from methanol/water had a m.p.=47°-48° C. Total yield=3.6 g (71 percent).

| Analysis:  | C     | H    | N    |
|------------|-------|------|------|
| Calculated | 57.15 | 2.78 | 3.51 |
| Found      | 56.80 | 2.72 | 3.63 |

E.
2-(3,5-Difluoro-4-hydroxyphenoxy)-3-fluoro-5-trifluoromethylpyridine

A mixture of the benzyloxyphenoxypyridine (3.4 g, 0.0085 mole) and acetic acid saturated with anhydrous HBr (50 ml) was warmed at 60°-70° C. for 30 minutes. The mixture was poured into water (300 ml) and the resulting mixture extracted with ether (2×200 ml). The combined ether extracts were washed with water (100 ml) then saturated sodium bicarbonate solution. After drying (MgSO$_4$) all the volatile material was evaporated. The resulting yellow solid was taken up in ether, treated with charcoal, then filtered through a short pad of silica gel. Removal of the solvent gave a light yellow solid (2.0 g, 76 percent). Recrystallization from methylcyclohexane gave colorless crystals: m.p.=125°-128° C. The NMR (CDCl$_3$) was consistent with the assigned structure.

| Analysis:  | C     | H    | N    |
|------------|-------|------|------|
| Calculated | 46.62 | 1.63 | 4.53 |
| Found      | 46.88 | 1.62 | 4.63 |

F. Methyl 2-(2,6-difluoro-4-((3-fluoro-5-trifluoromethylpyridinyl)-2-oxy)phenoxy)propanoate A stirred mixture of the pyridyloxyphenol (1.7 g, 0.0055 mole), methyl 2-bromopropanonate (0.92, 0.0055 mole), and potassium carbonate (0.83 g, 0.006 mole) in DMSO (15 ml) was heated at 70°-80° C. for two hours, cooled, and poured into ice water (200 ml). The resulting solution was acidified with HCl, then extracted with ether (2×100 ml). The ether phases were combined, treated with charcoal then filtered through a short pad of silica gel. The solvent was evaporated to give the desired pyridyloxy-phenoxypropanoate as a light yellow oil (1.7 g, 78 percent): R.I.=1.4828 @ 25° C.; NMR (CDCL$_3$) was consistent with the assigned structure.

| Analysis:  | C     | H    | N    |
|------------|-------|------|------|
| Calculated | 48.62 | 2.81 | 3.54 |
| Found      | 48.69 | 2.82 | 3.65 |

EXAMPLE 6

Following the procedure of Example 5, except for employing 2,6-dichloroquinoxaline instead of the pyridine reactants of Example 5, the compound methyl 2-(2,6-difluoro-4-((6-chloroquinoxaline)-3-oxy)phenoxy)propanoate was prepared. M.P. 111.5°-112° C.

| Analysis:  | C     | H    | N    |
|------------|-------|------|------|
| Calculated | 54.76 | 3.32 | 7.10 |
| Found      | 54.48 | 3.25 | 7.13 |

NMR ($^1$H, $^{19}$F) was consistent with the assigned structure.

EXAMPLE 7

Propanoic acid: 2-(4-(3-chloro-5-trifluoromethyl-2-pyridyloxy)-2-fluorophenoxy)

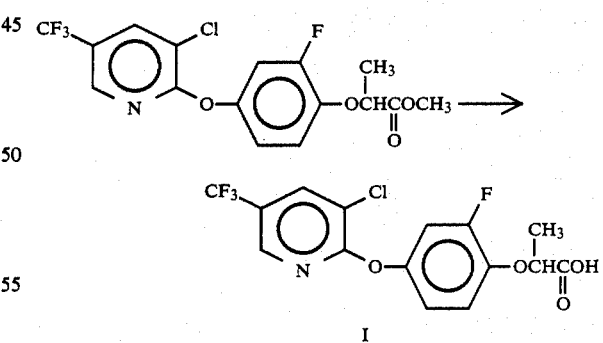

Methyl 2-(4-(3-chloro-5-trifluoromethyl-2-pyridyloxy)-2-fluorophenoxy)propanoate (46.2 g, 0.117 mole) was added to a solution of potassium hydroxide (7.9 g, 0.14 mole) and ethanol (125 ml). This mixture was stirred for one hour at reflux. The ethanol was subsequently removed by distillation, followed by addition of water (100 ml) to the pasty residue. While cooling below 10° C., aqueous HCl (6N) was added until a ph=6 was reached. The solid which separated was extracted into ether. The ether phases were combined, washed with water, dried (MgSO4) and the ether evaporated to give 41.5 g (93%) of the desired acid as a white solid. An analytical sample, prepared by trituration of this solid with hot water, filtering and drying in a vacuum oven at 50° for 12 hours, had a melting point of 128°–129° C.

| Analysis: | C | H | N |
|---|---|---|---|
| Calculated | 47.44 | 2.66 | 3.69 |
| Found | 47.54 | 2.60 | 3.77 |

EXAMPLE 8

2-(4-(3-chloro-5-trifluoromethyl-2-pyridyloxy)-2-fluorophenoxy)propanoyl chloride Thionyl chloride (7.24 g, 0.0608 mole) was added to a stirred solution of 2-(4-(3-chloro-5-trifluoromethyl-2-pyridyloxy)-2-fluorophenoxy)propanoic acid (21.0 g, 0.0553 mole), benzene (150 ml), and dimethyl formamide (0.3 g). Refluxing was effected for three hours. The benzene and residual thionyl chloride were removed by distillation under vacuum. The resulting amber colored oil (21 g) was shown to be the desired acid chloride by NMR and IR spectroscopy. This material was used directly in subsequent reactions.

EXAMPLE 9

Propanoic acid: 2-(4-(3-chloro-5-trifluoromethyl-2-pyridyloxy)-2-fluorophenoxy), n-butyl ester During a five minute period, a solution of the previously prepared acid chloride (Example 8) (1.7 g, 4.27 mmole) in diethyl ether (10.0 ml) was added to a stirred, room temperature solution of n-butanol (0.332 g, 4.48 mmole), pyridine (0.355 g, 4.48 mmole), 4-dimethylaminopyridine (catalytic amount), and diethyl ether (40 ml). After 19 hours, the above mixture was poured into a 2N HCl solution (100 ml) and shaken. On separation of the ether phase from that of the aqueous, the latter was discarded. The etheral solution was then washed with water (3×50 ml), decolorized with charcoal, dried (MgSO4), and then filtered through a short column of silica gel. The solvent was evaporated to give the desired ester as an amber oil (1.5 g, 80.6%). Refractive Index=1.5000 @ 25° C.

| Analysis: | C | H | N |
|---|---|---|---|
| Calculated | 52.36 | 4.17 | 3.09 |
| Found | 52.40 | 4.09 | 3.35 |

In a manner similar to the synthesis of Example 9, the following derivatives were prepared:

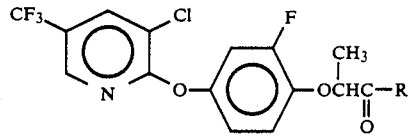

| R | Refractive Index (25° C.) | % Yield |
|---|---|---|
| —O—⟨⟩—Cl | 1.5448 | 69 |

| Analysis: | C | H | N |
|---|---|---|---|
| Calculated | 51.44 | 2.68 | 2.86 |
| Found | 51.48 | 2.50 | 2.94 |

| R | Refractive Index (25° C.) | % Yield |
|---|---|---|
| —O(CH2)7CH3 | 1.4926 | 73 |

| Analysis: | C | H | N |
|---|---|---|---|
| Calculated | 56.15 | 5.34 | 2.85 |
| Found | 56.20 | 5.14 | 2.90 |

| R | Refractive Index (25° C.) | % Yield |
|---|---|---|
| —S—CH(CH3)2 | 1.5263 | 55 |

| Analysis: | C | H | N |
|---|---|---|---|
| Calculated | 49.37 | 3.69 | 3.20 |
| Found | 50.19 | 3.66 | 3.28 |

EXAMPLE 10

Propanoic acid: 2-(4-(3-chloro-5-trifluoromethyl-2-pyridyloxy)-2-fluorophenoxy)-, amide A solution of the acid chloride of Example 8 (2.0 g, 5.02 mmole) in ether (10 ml), was added all at once to a vigorously stirred solution of concentrated ammonium hydroxide (50 ml). The reaction mixture was stirred for one hour at room temperature, then ether (100 ml) was added. The organic phase was separated, washed with water, treated with charcoal, dried (MgSO4), then filtered through a short column of silica gel. Evaporation of the solvent gave the desired amide (1.5 g, 79%) as a white solid: m.p.=136°–137° C.

| Analysis: | C | H | N |
|---|---|---|---|
| Calculated | 47.57 | 2.93 | 7.40 |
| Found | 47.50 | 2.80 | 7.61 |

EXAMPLE 11

Propanoic acid: 2-(4-(3-chloro-5-trifluoromethyl-2-pyridyloxy)-2-fluorophenoxy)-, amide, N-2,6-difluorophenyl During a five minute period, a solution of the acid chloride of Example 8 (2.0 g, 5.02 mmole) in ether (10 ml) was added to a stirred, room temperature solution of 2,6-difluoroaniline (0.65 g, 5.02 mmole), triethyl amine (0.55 g, 5.5. mmole) and diethyl ether (40 ml). Stirring was continued for 19 hours. The solution was then poured into a 100 ml of 2N HCl and shaken. The ether layer was then separated from the aqueous layer, and the latter discarded. The ether solution was washed with water (2×50 ml), decolorized with charcoal, dried (MgSO4), filtered through a short column of silica gel, and the solvent evaporated. This gave the desired amide (1.5 g, 61%) as a white solid: m.p.=161°–162° C.

| Analysis: | C | H | N |
|---|---|---|---|
| Calculated | 51.39 | 2.68 | 5.71 |

| Analysis: | C | H | N |
|---|---|---|---|
| Found | 51.22 | 2.65 | 5.73 |

In manner similar to the synthesis of Example 11, the following derivatives were prepared:

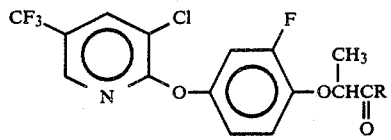

| R | Melting Point | % Yield | Analysis: | C | H | N |
|---|---|---|---|---|---|---|
| —NH—⟨⟩—CF₃ | 125.5–127° C. | 69% | Calculated<br>Found | 50.54<br>50.62 | 2.70<br>2.64 | 5.36<br>5.55 |
| —NH—CH₂CH=CH₂ | 82–82.5° C. | 62% | Calculated<br>Found | 51.62<br>51.67 | 3.62<br>3.47 | 6.19<br>7.02 |
| R | Refractive Index | % Yield | Analysis: | C | H | N |
| —NH—CH—COCH₃<br>     |<br>     CH<br>    /  \\<br>CH₃  CH₃ | 1.5082<br>@ 25° C. | 85% | Calculated<br>Found | 51.17<br>51.15 | 4.30<br>4.26 | 5.68<br>5.78 |
| —N(CH₂CH₃)₂ | 1.5187<br>@ 25° C. | 32% | Calculated<br>Found | 52.48<br>52.40 | 4.41<br>4.34 | 6.44<br>6.84 |

The compounds of the present invention have been found to be suitable for use in methods for the selective pre- and postemergent control of annual and perennial grassy weeds. These compounds, the active ingredients of the present invention, have been found to have advantage over prior art compounds in the control of annual and perennial grassy weeds in that the present compounds control such weeds at substantially lower dosage rates. In addition, the present compounds are sufficiently tolerant towards most broad leafed crops to contemplate control of grassy weeds therein at substantially commercially practicable levels, particularly so with the preferred compounds. In addition, certain of the compounds have sufficient tolerance towards cereal crops such as wheat to enable selective grassy weed control in these crops as well.

For such uses, unmodified active ingredients of the present invention can be employed. However, the present invention embraces the use of the compounds in composition form with an inert material, known in the art as an agricultural adjuvant or carrier, in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The herbicidally effective concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 parts of the additional compound(s).

The active ingredients of the present invention have been found to possess desirable herbicidal activity in general against grassy weeds such as foxtail, barnyardgrass, wild oats, seedling johnsongrass and crabgrass in preemergent operations and also against the same grasses in postemergent operations while being tolerant to important broadleaf crops such as cotton, soybeans, sugarbeets and rape and in the case of certain of the compounds, certain cereal crops such as wheat. These compounds are also uniquely effective in selectively controlling perennial grassy weeds such as johnsongrass, quackgrass, bermudagrass and dallisgrass.

The active ingredients of the present invention have been found to possess particularly desirable herbicidal activity against wild oats, foxtail, barnyardgrass, crabgrass and seedling johnsongrass in postemergent operations as well as desirable broad spectrum activity against the perennial grassy weeds listed above and at lower dosage rates than the substituted propanoates and propanols of the prior art while showing high selectivity to broadleaf crops and, in the case of certain of the compounds, wheat.

The exact rate to be applied is dependent not only on a specific active ingredient being applied, but also on a particular action desired, the plant species to be modified and the stage of growth thereof as well as the part of the plant to be contacted with the toxic active ingredient. Thus, all of the active ingredients of the present invention and compositions containing the same may not be equally effective at similar concentrations or against the same plant species.

In postemergent operations a dosage of about 0.05 to about 20 pounds/acre (0.056–22.4 kg/hectare) is generally applicable, although not all compounds are equally effective and some weeds are more difficult to control. Thus, a dosage rate in the range of about 0.01 to about 1.0 pound/acre (0.01–1.12 kg/hectare) is preferred in postemergent control of annual grassy weeds, while about 0.05 to about 5 pounds/acre (0.056–5.6 kg/hectare) is a preferred dosage range for the postemergent control of perennial grassy weeds. In applications to tolerant crops a weed controlling but less than crop damaging amount of from about 0.005 to about 1.0 lb/acre (0.0056 to 1.12 kgs/hectare) is generally employed.

In preemergent operations a dosage rate of 0.01 to 10 lbs/acre (0.011 to 11.2 kgs/hectare), preferably 0.05 to 2.0 lbs/acre (0.056 to 2.25 kgs/hectare) and most preferably 0.1 to 1 lb/acre (0.11 to 1.12 kgs/hectare) is generally employed.

The following examples illustrate effects of the compounds of this invention.

EXAMPLE 12

In representative operations, each compound to be utilized in a series of tests is dissolved in acetone to one-half of the final volume (twice the final concentration) to be used and the acetone solution in each case is admixed with an equal volume of water containing 0.1 percent by weight of the non-ionic surfactant TWEEN ®20 (a polyoxyethylene sorbitan monolaurate). The compositions, generally in the nature of an emulsion, were employed to spray separate respective plant species which had been grown to a height of 2–6 inches in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other portions of the plants were left untreated to serve as controls. After treatment, the plants were maintained for about two weeks under greenhouse conditions conducive for good plant growth and watered as necessary. The specific plant species, test compound and dosage and the percent postemergent control obtained are set forth in the table below. Control refers to the reduction in growth compared to the observed results of the same untreated species. Note the "NT" means "not tested".

Plant species in these tests were the following:

| Common Name | Scientific Name |
| --- | --- |
| Barnyardgrass (Watergrass) | *Echinochloa crusgalli* |
| Crabgrass | *Digitaria sanquinalis* |
| Yellow foxtail | *Setaria lutescens* |
| Johnson grass | *Sorghum halepense* |
| Wild Oats | *Avena fatua* |

POSTEMERGENT CONTROL OF PLANT SPECIES

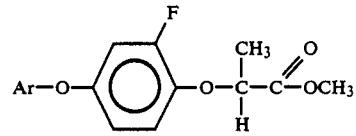

General structure: Ar—O—(3-fluorophenyl)—O—CH(CH$_3$)—C(=O)—OCH$_3$

| Ar | Plant Species | Percent Control at Indicated Dosage (ppm) | | | | | |
| --- | --- | --- | --- | --- | --- | --- | --- |
| | | 250 | 125 | 62.5 | 31.25 | 15.6 | 7.8 |
| 3-CF$_3$, 6-Cl, 2-methyl pyridin-5-yl | Barnyardgrass | 100 | 100 | 100 | 100 | 65 | 10 |
| | Crabgrass | 100 | 100 | 100 | 100 | 100 | 100 |
| | Foxtail | 100 | 100 | 100 | 100 | 100 | 60 |
| | Johnsongrass | 100 | 100 | 100 | 100 | 100 | 100 |
| | Wild Oats | 100 | 100 | 100 | 100 | 20 | 0 |
| 3-Cl, 5-F, 2-methyl pyridin-6-yl | Barnyardgrass | NT | 100 | 100 | 100 | 100 | 10 |
| | Crabgrass | NT | 100 | 100 | 100 | 100 | 100 |
| | Foxtail | NT | 100 | 100 | 100 | 100 | 95 |
| | Johnsongrass | NT | 100 | 100 | 100 | 100 | 95 |
| | Wild Oats | NT | 99 | 100 | 100 | 85 | 0 |
| Chloro-methyl pyrazinyl | Barnyardgrass | NT | 100 | 100 | 100 | 100 | 100 |
| | Crabgrass | NT | 100 | 100 | 100 | 100 | 100 |
| | Foxtail | NT | 100 | 100 | 100 | 90 | 20 |
| | Johnsongrass | NT | 100 | 100 | 100 | 100 | 60 |
| | Wild Oats | NT | 95 | 50 | 40 | 10 | 0 |

POSTEMERGENT CONTROL OF PLANT SPECIES

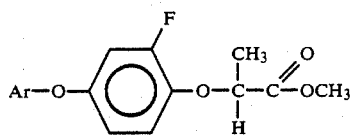

| Ar | Plant Species | Percent Control at Indicated Dosage (ppm) | | | | | |
|---|---|---|---|---|---|---|---|
| | | 250 | 125 | 62.5 | 31.25 | 15.6 | 7.8 |
| CF$_3$, F pyridine (2-methyl) | Barnyardgrass | NT | 100 | 100 | 100 | 100 | 100 |
| | Crabgrass | NT | 100 | 100 | 100 | 100 | 100 |
| | Foxtail | NT | 100 | 100 | 100 | 100 | 100 |
| | Johnsongrass | NT | 100 | 100 | 100 | 100 | 100 |
| | Wild Oats | NT | 100 | 100 | 100 | 35 | 0 |
| Cl-quinoline | Barnyardgrass | 100 | 100 | 100 | 100 | 100 | 0 |
| | Crabgrass | 100 | 100 | 100 | 90 | 80 | 20 |
| | Foxtail | 100 | 100 | 100 | 80 | NT | 0 |
| | Johnsongrass | 100 | 100 | 100 | 100 | 100 | 100 |
| | Wild Oats | 98 | 80 | 30 | 20 | 0 | 0 |
| I-pyrazine | Barnyardgrass | 100 | 100 | 100 | 98 | 0 | 0 |
| | Crabgrass | 100 | 98 | 98 | 80 | 80 | NT |
| | Foxtail | 100 | 100 | 80 | 70 | 60 | NT |
| | Johnsongrass | 100 | 98 | 98 | 0 | 0 | 0 |
| | Wild Oats | 98 | 50 | 50 | 0 | 0 | 0 |
| Br, F phenyl (methyl) | Barnyardgrass | 100 | 100 | 100 | 100 | 0 | 0 |
| | Crabgrass | 100 | 100 | 100 | 100 | 95 | 0 |
| | Foxtail | 100 | 100 | 90 | 75 | 75 | 0 |
| | Johnsongrass | 35 | 20 | 10 | 0 | 0 | 0 |
| | Wild Oats | 40 | 20 | 0 | 0 | 0 | 0 |
| CF$_3$-pyridine | Barnyardgrass | NT | 100 | 100 | 100 | 98 | 90 |
| | Crabgrass | NT | 100 | 100 | 100 | 100 | NT |
| | Foxtail | NT | 100 | 95 | 95 | 90 | 80 |
| | Johnsongrass | NT | 100 | 100 | 100 | 100 | 70 |
| | Wild Oats | NT | 98 | 98 | NT | NT | 0 |
| Cl, Cl pyridine (2-methyl) | Barnyardgrass | 100 | 100 | 100 | 100 | 0 | 0 |
| | Crabgrass | 100 | 100 | 100 | 100 | 100 | NT |
| | Foxtail | 100 | 100 | 100 | 100 | 100 | NT |
| | Johnsongrass | 100 | 100 | 100 | 100 | 100 | NT |
| | Wild Oats | 100 | 100 | 100 | 100 | 100 | NT |

POSTEMERGENT CONTROL OF PLANT SPECIES

CF$_3$—(pyridine-Cl)—O—(phenyl-F)—O—C(CH$_3$)(H)—Z

| Z | Plant Species | Percent Control at Indicated Dosage (ppm) | | | | | |
|---|---|---|---|---|---|---|---|
| | | 62.5 | 31.25 | 15.63 | 7.8 | 3.9 | 1.9 |
| —CONH$_2$ | Barnyardgrass | 100 | 100 | 100 | 100 | 100 | 50 |
| | Crabgrass | 100 | 100 | 100 | 100 | 100 | 40 |
| | Johnsongrass | 100 | 100 | 100 | 80 | 100 | 0 |
| | Wild Oats | 100 | 100 | 100 | 100 | 90 | 0 |
| | Yellow Foxtail | 100 | 100 | 100 | 100 | 100 | 50 |
| —CONHCH$_2$CH=CH$_2$ | Barnyardgrass | 100 | 100 | 100 | 100 | 100 | 100 |
| | Crabgrass | 100 | 100 | 100 | 100 | 90 | 100 |
| | Johnsongrass | 100 | 100 | 100 | 100 | 70 | 80 |
| | Wild Oats | 100 | 100 | 100 | 100 | 95 | 0 |
| | Yellow Foxtail | 100 | 100 | 100 | 100 | 85 | 0 |
| —CON(C$_2$H$_5$)$_2$ | Barnyardgrass | 100 | 100 | 100 | 100 | 50 | 0 |
| | Crabgrass | 100 | 100 | 100 | 100 | 80 | 10 |
| | Johnsongrass | 100 | 100 | 90 | 80 | 0 | 0 |
| | Wild Oats | 100 | 100 | 100 | 60 | 40 | 0 |
| | Yellow Foxtail | 100 | 100 | 100 | 80 | 30 | 0 |
| —COSCH(CH$_3$)$_2$ | Barnyardgrass | 100 | 100 | 100 | 100 | 100 | 70 |
| | Crabgrass | 100 | 100 | 100 | 100 | 100 | 90 |
| | Johnsongrass | 100 | 100 | 100 | 100 | 80 | 70 |

-continued

POSTEMERGENT CONTROL OF PLANT SPECIES

| Z | Plant Species | Percent Control at Indicated Dosage (ppm) | | | | | |
|---|---|---|---|---|---|---|---|
| | | 62.5 | 31.25 | 15.63 | 7.8 | 3.9 | 1.9 |
| | Wild Oats | 100 | 100 | 100 | 100 | 65 | 40 |
| | Yellow Foxtail | 100 | 100 | 100 | 100 | 100 | 50 |
| —CONH—(2,6-difluorophenyl) | Barnyardgrass | 100 | 100 | 100 | 100 | 80 | 60 |
| | Crabgrass | 100 | 100 | 100 | 100 | 90 | 30 |
| | Johnsongrass | 100 | 100 | 100 | 100 | 60 | 40 |
| | Wild Oats | 100 | 100 | 100 | 80 | 50 | 0 |
| | Yellow Foxtail | 100 | 100 | 100 | 100 | 70 | 0 |
| —CO(CH$_2$)$_7$CH$_3$ | Barnyardgrass | 100 | 100 | 100 | 100 | 100 | 100 |
| | Crabgrass | 100 | 100 | 100 | 100 | 90 | 100 |
| | Johnsongrass | 100 | 100 | 100 | 90 | 90 | 0 |
| | Wild Oats | 100 | 100 | 100 | 100 | 0 | 0 |
| | Yellow Foxtail | 100 | 100 | 100 | 100 | 70 | 20 |
| —CONH—(4-CF$_3$-phenyl) | Barnyardgrass | 100 | 100 | 100 | 100 | 100 | 0 |
| | Crabgrass | 100 | 100 | 100 | 100 | 90 | 70 |
| | Johnsongrass | 100 | 100 | 100 | 90 | 25 | 0 |
| | Wild Oats | 40 | 50 | 20 | 0 | 0 | 0 |
| | Yellow Foxtail | 100 | 100 | 100 | 100 | 0 | 0 |
| —COO—(4-Cl-phenyl) | Barnyardgrass | 100 | 100 | 100 | 100 | 100 | 100 |
| | Crabgrass | 100 | 100 | 100 | 100 | 100 | 100 |
| | Johnsongrass | 100 | 100 | 100 | 100 | 85 | 40 |
| | Wild Oats | 100 | 100 | 100 | 60 | 60 | 60 |
| | Yellow Foxtail | 100 | 100 | 100 | 100 | 100 | 0 |
| —COO(CH$_2$)$_3$CH$_3$ | Barnyardgrass | 100 | 100 | 100 | 100 | 100 | 80 |
| | Crabgrass | 100 | 100 | 100 | 100 | 100 | 100 |
| | Johnsongrass | 100 | 100 | 100 | 100 | 85 | 90 |
| | Wild Oats | 100 | 100 | 100 | 100 | 90 | 0 |
| | Yellow Foxtail | 100 | 100 | 100 | 100 | 100 | 35 |
| —COOH | Barnyardgrass | 100 | 100 | 100 | 100 | 100 | 50 |
| | Crabgrass | 100 | 100 | 100 | 100 | 100 | 30 |
| | Johnsongrass | 100 | 100 | 100 | 100 | 95 | 40 |
| | Wild Oats | 100 | 100 | 100 | 90 | 40 | 20 |
| | Yellow Foxtail | 100 | 100 | 100 | 100 | 90 | 30 |
| —CONHCHCOOCH$_3$ with CH$_3$—C(H)—CH$_3$ | Barnyardgrass | 100 | 100 | 100 | 100 | 80 | 20 |
| | Crabgrass | 100 | 100 | 90 | 100 | 60 | 0 |
| | Johnsongrass | 100 | 100 | 100 | 90 | 30 | 0 |
| | Wild Oats | 100 | 100 | 85 | 20 | 0 | 0 |
| | Yellow Foxtail | 100 | 100 | 100 | 60 | 0 | 0 |

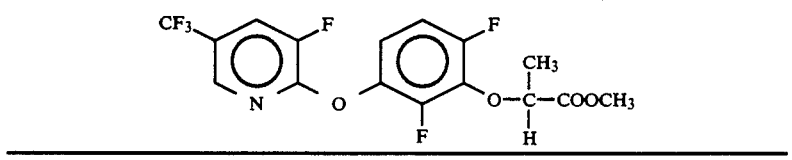

| | | | | | |
|---|---|---|---|---|---|
| Barnyardgrass | 100 | 100 | 100 | 100 | |
| Crabgrass | 100 | 100 | 100 | 100 | |
| Johnsongrass | 100 | 100 | 98 | 95 | |
| Wild Oats | 100 | 100 | 100 | 100 | |
| Yellow Foxtail | 95 | 90 | 85 | 80 | |

(Structure: Cl-phenyl-N=CH-C(=N)-O-(2,6-difluorophenyl)-O-C(CH$_3$)(H)-COOCH$_3$)

| | | | | |
|---|---|---|---|---|
| Barnyardgrass | 0 | 0 | 0 | 0 |
| Crabgrass | 100 | 70 | 80 | 50 |
| Johnsongrass | 0 | 0 | 0 | 0 |
| Wild Oats | 100 | 0 | 0 | 0 |
| Yellow Foxtail | 0 | 0 | 0 | 0 |

EXAMPLE 13

So as to clearly illustrate the phytotoxic properties of the various active ingredients of the present invention applied preemergently, a controlled greenhouse experiment is described below.

The seeds of various species of plants were planted in beds of good agricultural soil in a greenhouse. A number of compositions of the present invention, generally in the nature of an aqueous emulsion, were applied at rates listed in the table so as to deposit a predetermined amount of active ingredients uniformly throughout the surface of the bed. Another seed bed was treated only with water to serve as a control. After treatment, the seed beds were maintained for two weeks under greenhouse conditions conductive for good plant growth and watered as necessary. The specific plant species, test compound, and dosage and the percent preemergent control are set forth in the table below. Control refers to the reduction in growth compared to the observed results of the same untreated species.

PREEMERGENT CONTROL OF PLANT SPECIES

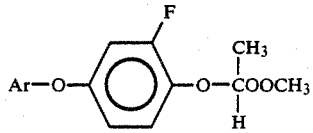

| Ar | Plant Species | Percent Control at Indicated Dosage (lb/acre, kg/hectare) | | | | |
|---|---|---|---|---|---|---|
| | | 0.5 (0.56) | 0.25 (0.28) | 0.125 (0.14) | 0.063 (0.07) | 0.031 (0.035) |
| 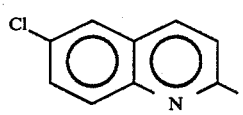 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 0 | 0 | 0 | 0 | 0 |
| | Wheat | 0 | 0 | 0 | 0 | 0 |
| | Barnyardgrass | 100 | 50 | 20 | 0 | 0 |
| | Johnsongrass | 100 | 70 | 0 | 0 | 0 |
| | Wild Oats | 40 | 30 | 0 | 0 | 0 |
| | Yellow Foxtail | 100 | 40 | 0 | 0 | 0 |
| 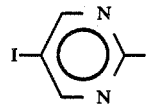 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 0 | 0 | 0 | 0 |
| | Wheat | 0 | 0 | 0 | 0 | 0 |
| | Barnyardgrass | 60 | 10 | 0 | 0 | 0 |
| | Johnsongrass | 100 | 100 | 40 | 0 | 0 |
| | Wild oats | 100 | 0 | 0 | 0 | 0 |
| | Yellow Foxtail | 100 | 100 | 0 | 0 | 0 |
| 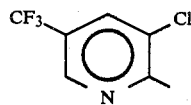 | Cotton | NT | 0 | 0 | 0 | 0 |
| | Rape | NT | 0 | 0 | 0 | 0 |
| | Soybean | NT | 0 | 0 | 0 | 0 |
| | Sugarbeet | NT | 0 | 0 | 0 | 0 |
| | Rice | NT | 100 | 100 | 75 | 10 |
| | Wheat | NT | 100 | 85 | 40 | 0 |
| | Barnyardgrass | NT | 100 | 100 | 70 | 15 |
| | Johnsongrass | NT | 100 | 100 | 100 | 95 |
| | Wild Oats | NT | 100 | 95 | 50 | 15 |
| | Yellow Foxtail | NT | 100 | 100 | 100 | 80 |
| 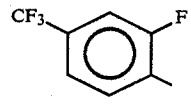 | Cotton | NT | 0 | 0 | 0 | 0 |
| | Rape | NT | 0 | 0 | 0 | 0 |
| | Soybean | NT | 0 | 0 | 0 | 0 |
| | Sugarbeet | NT | 0 | 0 | 0 | 0 |
| | Rice | NT | 100 | 90 | 70 | 20 |
| | Wheat | NT | 70 | 0 | 0 | 0 |
| | Barnyardgrass | NT | 100 | 75 | 30 | 0 |
| | Johnsongrass | NT | 100 | 100 | 25 | 0 |
| | Wild oats | NT | 85 | 80 | 25 | 0 |
| | Yellow Foxtail | NT | 100 | 100 | 20 | 0 |
| 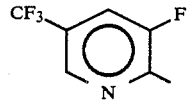 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 100 | 100 | 95 | 50 |
| | Wheat | 100 | 100 | 100 | 80 | 0 |
| | Barnyardgrass | 100 | 100 | 100 | 60 | 50 |
| | Johnsongrass | 100 | 100 | 100 | 100 | 100 |
| | Wild Oats | 100 | 100 | 100 | 90 | 40 |
| | Yellow Foxtail | 100 | 100 | 100 | 100 | 90 |

-continued

PREEMERGENT CONTROL OF PLANT SPECIES

| | Plant Species | Percent Control at Indicated Dosage (lb/acre, kg/hectare) | | | | |
|---|---|---|---|---|---|---|
| | | 0.5 (0.56) | 0.25 (0.28) | 0.125 (0.14) | 0.063 (0.07) | 0.031 (0.035) |
| 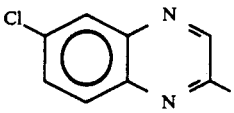 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 75 | 100 | 20 | 10 | 0 |
| | Wheat | 75 | 0 | 0 | 0 | 0 |
| | Barnyardgrass | 100 | 100 | 90 | 25 | 0 |
| | Johnsongrass | 100 | 100 | 100 | 40 | 0 |
| | Wild oats | 100 | 70 | 30 | 0 | 0 |
| | Yellow Foxtail | 100 | 100 | 40 | 0 | 0 |
| 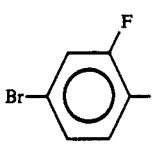 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 70 | 0 | 0 | 0 | 0 |
| | Wheat | 0 | 0 | 0 | 0 | 0 |
| | Barnyardgrass | 100 | 100 | 95 | 30 | 0 |
| | Johnsongrass | 99 | 40 | 0 | 0 | 0 |
| | Wild Oats | 90 | 30 | 10 | 0 | 0 |
| | Yellow Foxtail | 100 | 100 | 50 | 0 | 0 |
| 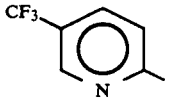 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 95 | 10 | 0 | 0 |
| | Wheat | 100 | 97 | 40 | 0 | 0 |
| | Barnyardgrass | 100 | 100 | 85 | 0 | 0 |
| | Johnsongrass | 100 | 95 | 75 | 0 | 0 |
| | Wild oats | 99 | 40 | 0 | 0 | 0 |
| | Yellow Foxtail | 100 | 100 | 100 | 0 | 0 |
| 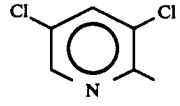 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 90 | 90 | 0 | 0 |
| | Wheat | 65 | 10 | 0 | 0 | 0 |
| | Barnyardgrass | 100 | 100 | 97 | 25 | NT |
| | Johnsongrass | 100 | 100 | 100 | 70 | NT |
| | Wild Oats | 100 | 100 | 100 | 80 | NT |
| | Yellow Foxtail | 100 | 99 | 100 | 0 | 0 |

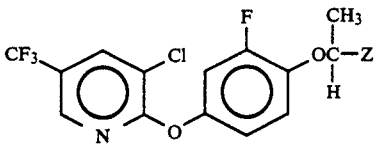

| Z | | | | | | |
|---|---|---|---|---|---|---|
| 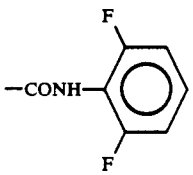 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 90 | 20 | 20 | 0 | 0 |
| | Wheat | 50 | 40 | 0 | 0 | 0 |
| | Barnyardgrass | 70 | 80 | 50 | 20 | 0 |
| | Johnsongrass | 95 | 85 | 30 | 30 | 0 |
| | Wild Oats | 90 | 20 | 0 | 0 | 0 |
| | Yellow Foxtail | 100 | 90 | 70 | 70 | 0 |
| —COSCH(CH$_3$)$_2$ | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 100 | 0 | 0 | 0 | 0 |
| | Rice | 100 | 90 | 0 | 0 | 0 |
| | Wheat | 100 | 100 | 90 | 0 | 0 |
| | Barnyardgrass | 90 | 90 | 50 | 0 | 0 |
| | Johnsongrass | 100 | 95 | 30 | 0 | 0 |
| | Wild Oats | 80 | 90 | 0 | 0 | 0 |
| | Yellow Foxtail | 100 | 90 | 50 | 0 | 0 |

-continued
PREEMERGENT CONTROL OF PLANT SPECIES

| | Plant Species | Percent Control at Indicated Dosage (lb/acre, kg/hectare) | | | | |
|---|---|---|---|---|---|---|
| | | 0.5 (0.56) | 0.25 (0.28) | 0.125 (0.14) | 0.063 (0.07) | 0.031 (0.035) |
| —CONH—⌬—CF₃ 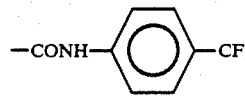 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 90 | 0 | 0 | 0 | 0 |
| | Wheat | 0 | 0 | 0 | 0 | 0 |
| | Barnyardgrass | 80 | 70 | 10 | 10 | 0 |
| | Johnsongrass | 70 | 70 | 60 | 0 | 0 |
| | Wild Oats | 0 | 0 | 0 | 0 | 0 |
| | Yellow Foxtail | 95 | 95 | 90 | 10 | 0 |
| —COO(CH₂)₂CH₃ | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 90 | 20 | 10 | 0 |
| | Wheat | 100 | 100 | 90 | 0 | 0 |
| | Barnyardgrass | 100 | 90 | 90 | 80 | 10 |
| | Johnsongrass | 95 | 90 | 60 | 60 | 60 |
| | Wild Oats | 100 | 85 | 50 | 20 | 10 |
| | Yellow Foxtail | 100 | 100 | 80 | 80 | 10 |
| —COOH | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 90 | 100 | 30 | 0 |
| | Wheat | 100 | 100 | 60 | 70 | 0 |
| | Barnyardgrass | 100 | 100 | 95 | 70 | 35 |
| | Johnsongrass | 100 | 100 | 90 | 70 | 45 |
| | Wild Oats | 100 | 100 | 70 | 70 | 0 |
| | Yellow Foxtail | 100 | 100 | 75 | 70 | 0 |
| —COO—⌬—Cl 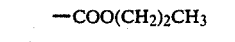 | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 100 | 80 | 90 | 10 |
| | Wheat | 100 | 90 | 50 | 20 | 0 |
| | Barnyardgrass | 95 | 95 | 80 | 85 | 10 |
| | Johnsongrass | 100 | 95 | 80 | 70 | 70 |
| | Wild Oats | 95 | 90 | 85 | 50 | 50 |
| | Yellow Foxtail | 100 | 95 | 90 | 0 | 0 |
| —COO(CH₂)₃CH₃ | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 100 | 80 | 75 | 0 |
| | Wheat | 100 | 100 | 0 | 0 | 0 |
| | Barnyardgrass | 100 | 95 | 90 | 75 | 20 |
| | Johnsongrass | 100 | 100 | 90 | 50 | 65 |
| | Wild Oats | 100 | 100 | 20 | 0 | 0 |
| | Yellow Foxtail | 100 | 100 | 95 | 70 | 30 |
| —CONH₂ | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 100 | 80 | 90 | 75 |
| | Wheat | 100 | 100 | 60 | 0 | 0 |
| | Barnyardgrass | 100 | 100 | 60 | 70 | 30 |
| | Johnsongrass | 90 | 95 | 80 | 70 | 70 |
| | Wild Oats | 100 | 100 | 80 | 70 | 60 |
| | Yellow Foxtail | 100 | 100 | 60 | 20 | 10 |
| —CONHCH(COOCH₃)CH(CH₃)₂  | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 100 | 100 | 90 | 45 |
| | Wheat | 100 | 90 | 0 | 0 | 0 |
| | Barnyardgrass | 100 | 90 | 90 | 70 | 30 |
| | Johnsongrass | 100 | 100 | 80 | 65 | 50 |
| | Wild Oats | 100 | 95 | 0 | 0 | 0 |
| | Yellow Foxtail | 100 | 100 | 70 | 70 | 0 |

-continued

| | PREEMERGENT CONTROL OF PLANT SPECIES | | | | | |
|---|---|---|---|---|---|---|
| | | Percent Control at Indicated Dosage (lb/acre, kg/hectare) | | | | |
| | Plant Species | 0.5 (0.56) | 0.25 (0.28) | 0.125 (0.14) | 0.063 (0.07) | 0.031 (0.035) |
| —CONHCH$_2$CH=CH$_2$ | Cotton | 0 | 0 | 0 | 0 | 0 |
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 100 | 90 | 0 | 0 | 0 |
| | Wheat | 50 | 0 | 0 | 0 | 0 |
| | Barnyardgrass | 100 | 100 | 60 | 0 | 0 |
| | Johnsongrass | 100 | 70 | 50 | 0 | 0 |
| | Wild Oats | 70 | 70 | 0 | 0 | 0 |
| | Yellow Foxtail | 100 | 100 | 80 | 50 | 0 |

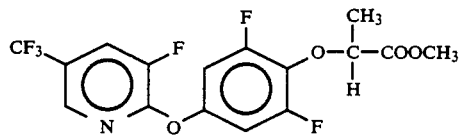

| | Cotton | NT | 0 | 0 | 0 | 0 |
|---|---|---|---|---|---|---|
| | Rape | NT | 0 | 0 | 0 | 0 |
| | Soybean | NT | 0 | 0 | 0 | 0 |
| | Sugarbeet | NT | 0 | 0 | 0 | 0 |
| | Rice | NT | 100 | 85 | 0 | 0 |
| | Wheat | NT | 60 | 95 | 20 | 0 |
| | Barnyardgrass | NT | 100 | 100 | 90 | 40 |
| | Johnsongrass | NT | 100 | 100 | 70 | 60 |
| | Wild Oats | NT | 100 | 93 | 80 | 0 |
| | Yellow Foxtail | NT | 100 | 100 | 60 | 50 |

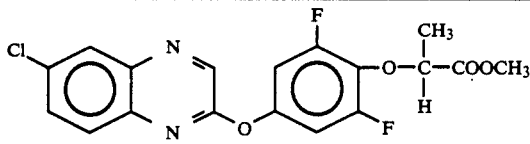

| | Cotton | 0 | 0 | 0 | 0 | 0 |
|---|---|---|---|---|---|---|
| | Rape | 0 | 0 | 0 | 0 | 0 |
| | Soybean | 0 | 0 | 0 | 0 | 0 |
| | Sugarbeet | 0 | 0 | 0 | 0 | 0 |
| | Rice | 80 | 0 | 0 | 0 | 0 |
| | Wheat | 0 | 0 | 0 | 0 | 0 |
| | Barnyardgrass | 85 | 60 | 50 | 0 | 0 |
| | Johnsongrass | 100 | 80 | 50 | 0 | 0 |
| | Wild oats | 90 | 0 | 0 | 0 | 0 |
| | Yellow Foxtail | 0 | 40 | 0 | 0 | 0 |

I claim:

1. A compound having the formula

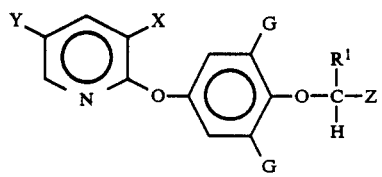

wherein X is halogen, Y is halogen, CF$_3$, CHF$_2$ or CClF$_2$, G is H or F with the proviso that at least one G is F, R$^1$ is a C$_1$–C$_3$ alkyl group, and Z is a carboxylic acid, or an agriculturally acceptable metallic or ammonium salt or lower alkyl ester thereof, or an R-enantiomer thereof.

2. Compound of claim 1 wherein X is Cl and Y is Cl.
3. Compound of claim 1 wherein X is F and Y is Cl.
4. Compound of claim 1 wherein X is Cl and Y is CF$_3$.
5. Compound of claim 1 wherein R$^1$ is CH$_3$ and Z is

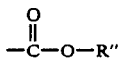

wherein R" is hydrogen, methyl, ethyl, propyl, isopropyl, isobutyl or n-butyl.

6. Compound of claim 4 wherein R$^1$ is CH$_3$ and Z is —COOH.
7. Compound of claim 5 wherein R$^1$ is CH$_3$ and Z is —COOCH$_3$.
8. Compound of claim 6 wherein R$^1$ is CH$_3$ and Z is —COOCH$_3$.
9. Compound of claim 1 wherein X is F and Y is CF$_3$.
10. Compound of claim 1 wherein R$^1$ is CH$_3$ and Z is —COOCH$_3$.
11. A compound having the formula

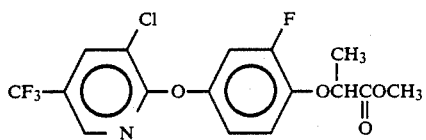

12. A compound having the formula

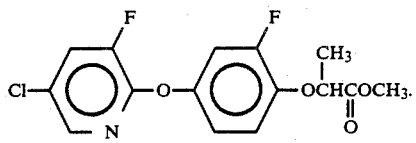

13. A compound having the formula

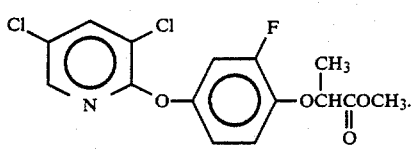

14. A compound having the formula

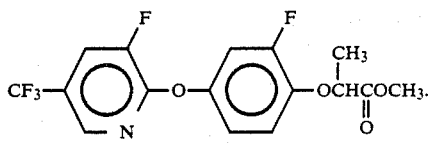

15. A method of killing and/or controlling undesired grassy plants which comprises providing in said grassy plants a herbicidally effective amount of a compound having the formula

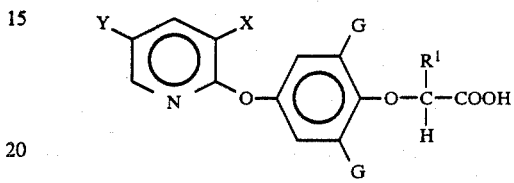

wherein X is halogen, Y is halogen, $CF_3$, $CHF_2$ or $CClF_2$, G is H or F with the proviso that at least one G is F, and $R^1$ is a $C_1$-$C_3$ alkyl group.

* * * * *